United States Patent
Chen et al.

(10) Patent No.: US 10,534,957 B2
(45) Date of Patent: *Jan. 14, 2020

(54) EYEBALL MOVEMENT ANALYSIS METHOD AND DEVICE, AND STORAGE MEDIUM

(71) Applicant: Ping An Technology (Shenzhen) Co., Ltd., Shenzhen, Guangdong (CN)

(72) Inventors: Lin Chen, Guangdong (CN); Guohui Zhang, Guangdong (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,457

(22) PCT Filed: Oct. 31, 2017

(86) PCT No.: PCT/CN2017/108748
§ 371 (c)(1),
(2) Date: Mar. 29, 2019

(87) PCT Pub. No.: WO2019/033569
PCT Pub. Date: Feb. 21, 2019

(65) Prior Publication Data
US 2019/0362144 A1    Nov. 28, 2019

(30) Foreign Application Priority Data
Aug. 17, 2017   (CN) .......................... 2017 1 0709112

(51) Int. Cl.
*G06K 9/00* (2006.01)
*G06F 3/01* (2006.01)
(Continued)

(52) U.S. Cl.
CPC ............ *G06K 9/00604* (2013.01); *A61B 3/14* (2013.01); *G06F 3/013* (2013.01);
(Continued)

(58) Field of Classification Search
None
See application file for complete search history.

(56) References Cited

U.S. PATENT DOCUMENTS

2004/0005083 A1* 1/2004 Fujimura ............... A61B 3/113
                                                     382/103
2014/0096077 A1* 4/2014 Jacob ..................... G06F 3/013
                                                     715/810
(Continued)

FOREIGN PATENT DOCUMENTS

CN          101706872 A      5/2010
CN          101984453 A      3/2011
(Continued)

OTHER PUBLICATIONS

International Search Report of PCT Patent Application No. PCT/CN2017/108748 dated May 23, 2018.
(Continued)

*Primary Examiner* — Jiangeng Sun (57) ABSTRACT

The application discloses an eyeball movement analysis method and device and a storage medium. The method includes: acquiring a real-time image shot by a photographic device and extracting a real-time facial image from the real-time image; inputting the real-time facial image into a pretrained eye mean shape and recognizing $n_1$ orbit feature points and $n_2$ eyeball feature points representative of an eye position in the real-time facial image; determining an eye region according to the ($n_1+n_2$) feature points and judging whether the eye region is a human eye region or not by use of a human eye classification model; and if YES, calculating a movement direction and movement distance of an eyeball in the real-time facial image according to x and y coordinates of the $n_1$ orbit feature points and $n_2$ eyeball feature points in the real-time facial image.

9 Claims, 4 Drawing Sheets

(51) Int. Cl.
*A61B 3/14* (2006.01)
*A61B 3/113* (2006.01)
(52) U.S. Cl.
CPC .......... *G06K 9/00617* (2013.01); *A61B 3/113* (2013.01); *G06K 9/0061* (2013.01)

(56) References Cited

U.S. PATENT DOCUMENTS

| | | | | |
|---|---|---|---|---|
| 2015/0338651 | A1* | 11/2015 | Wang | G06F 1/163 |
| | | | | 345/8 |
| 2018/0018451 | A1* | 1/2018 | Spizhevoy | G06N 3/04 |
| 2018/0126901 | A1* | 5/2018 | Levkova | B60Q 9/00 |
| 2018/0271364 | A1* | 9/2018 | Orlosky | A61B 3/113 |

FOREIGN PATENT DOCUMENTS

| | | | |
|---|---|---|---|
| CN | 102073435 A | 5/2011 | |
| CN | 105069745 A | 11/2015 | |

OTHER PUBLICATIONS

1st Office Action of counterpart Chinese Patent Application No. 201710709112.8 dated Jun. 4, 2018.
Notification to Grant Patent Right of counterpart Chinese Patent Application No. 201710709112.8 dated Aug. 15, 2018.
Yu, Dengmiao, Eye Control System Based on OpenCv and MFC of PC Side, Chinese Master's Theses Full-text Database—Information and Technology, Mar. 15, 2016, Issue 3, pp. 11-13 and 32-38.

* cited by examiner

EYEBALL MOVEMENT ANALYSIS METHOD AND DEVICE, AND STORAGE MEDIUM

CLAIM OF PRIORITY

This application is based on the Paris Convention and claims priority to China Patent Application No. CN201710709112.8, filed on Aug. 17, 2017 and entitled "Eyeball Movement Analysis Method and Device, and Storage Medium", which is hereby incorporated by reference in its entirety.

TECHNICAL FIELD

The application relates generally to the technical field of computer vision processing, and more particularly relates to an eyeball movement analysis method and device, and a computer-readable storage medium.

BACKGROUND

Eyeball movement capturing is a biological recognition technology for recognizing an eye movement of a user on the basis of facial feature information of the user. At present, eyeball movement capturing is applied to extensive fields, plays a very important role in many fields of financial payment, access control and attendance, identity recognition and the like and brings great convenience to people's lives. For a product, a method is usually to detect an electric field change about an eyeball by use of professional equipment so as to capture the eyeball or to recognize a change in an iris angle by use of camera equipment to track the eyeball.

However, the above two methods both have shortcomings. For the first method, the professional equipment is required to be worn and there is a strict requirement on an environment. For the second method, during iris detection, a human eye is required to be relatively close to a camera and the method is low in iris detection speed and unsuitable for a real-time condition.

SUMMARY

The application provides an eyeball movement analysis method and device and a computer-readable storage medium, which mainly aim at calculating movement information of an eyeball in a real-time facial image according to a coordinate of an eye feature point to implement analysis about an eye region and real-time capturing of an eyeball movement.

In order to achieve the foregoing objective, the application provides an electronic device, which includes a memory, a processor and a photographic device, the memory including an eyeball movement analysis program and the eyeball movement analysis program being executed by the processor to implement the following steps of:

a real-time facial image acquisition step: acquiring a real-time image shot by the photographic device and extracting a real-time facial image from the real-time image by use of a face recognition algorithm;

a feature point recognition step: inputting the real-time facial image into a pretrained eye mean shape and recognizing $n_1$ orbit feature points and $n_2$ eyeball feature points representative of an eye position in the real-time facial image by use of the eye mean shape;

a human eye region recognition step: determining an eye region according to the $n_1$ orbit feature points and the $n_2$ eyeball feature points, inputting the eye region into a pretrained human eye classification model and judging whether the eye region is a human eye region or not; and an eyeball movement judgment step: if the eye region is a human eye region, calculating a movement direction and movement distance of an eyeball in the real-time facial image according to x and y coordinates of the $n_1$ orbit feature points and $n_2$ eyeball feature points in the real-time facial image.

Preferably, the eyeball movement judgment step includes:

calculating a center coordinate of an orbit in the real-time facial image according to the x and y coordinates of the $n_1$ orbit feature points; and calculating a positional relationship between a center of the orbit and each eyeball feature point to judge the movement direction and movement distance of the eyeball.

Preferably, the eyeball movement analysis program is executed by the processor to further implement the following step:

a prompting step: when the human eye classification model judges that the eye region is not a human eye region, making such a prompt that no human eye region is detected in the present real-time image and no eyeball movement can be judged, and returning to the real-time image capturing step to capture a next real-time image.

Preferably, training steps for the human eye classification model include:

collecting m human eye positive sample images and m human eye negative sample images;

extracting local features of each human eye positive sample image and human eye negative sample image; and training a Support Vector Machine (SVM) by use of the human eye positive sample images, the human eye negative sample images and the local features thereof to obtain the human eye classification model.

Preferably, training steps for the eye mean shape include:

establishing a first sample library with n facial images and marking $n_1$ orbit feature points and $n_2$ eyeball feature points in each facial image in the first sample library, the $(n_1+n_2)$ feature points in each facial image forming a shape feature vector S to obtain n shape feature vectors S of an eye; and training a facial feature recognition model by use of the n shape feature vectors S to obtain the eye mean shape about faces.

In addition, in order to achieve the foregoing objective, the application also provides an eyeball movement analysis method, which includes:

a real-time facial image acquisition step: acquiring a real-time image shot by a photographic device and extracting a real-time facial image from the real-time image by use of a face recognition algorithm;

a feature point recognition step: inputting the real-time facial image into a pretrained eye mean shape and recognizing $n_1$ orbit feature points and $n_2$ eyeball feature points representative of an eye position in the real-time facial image by use of the eye mean shape;

a human eye region recognition step: determining an eye region according to the $n_1$ orbit feature points and the $n_2$ eyeball feature points, inputting the eye region into a pretrained human eye classification model and judging whether the eye region is a human eye region or not; and an eyeball movement judgment step: if the eye region is a human eye region, calculating a movement direction and movement distance of an eyeball in the real-time facial image according to x and y coordinates of the $n_1$ orbit feature points and $n_2$ eyeball feature points in the real-time facial image.

Preferably, the eyeball movement judgment step includes:

calculating a center coordinate of an orbit in the real-time facial image according to the x and y coordinates of the $n_1$ orbit feature points; and calculating a positional relationship between a center of the orbit and each eyeball feature point to judge the movement direction and movement distance of the eyeball.

Preferably, the method further includes:

a prompting step: when the human eye classification model judges that the eye region is not a human eye region, making such a prompt that no human eye region is detected in the present real-time image and no eyeball movement can be judged, and returning to the real-time image capturing step to capture a next real-time image.

Preferably, training steps for the human eye classification model include:

collecting m human eye positive sample images and m human eye negative sample images;

extracting local features of each human eye positive sample image and human eye negative sample image; and training an SVM by use of the human eye positive sample images, the human eye negative sample images and the local features thereof to obtain the human eye classification model.

Preferably, training steps for the eye mean shape include:

establishing a first sample library with n facial images and marking $n_1$ orbit feature points and $n_2$ eyeball feature points in each facial image in the first sample library, the $(n_1+n_2)$ feature points in each facial image forming a shape feature vector S to obtain n shape feature vectors S of an eye; and training a facial feature recognition model by use of the n shape feature vectors S to obtain the eye mean shape about faces.

Moreover, in order to achieve the foregoing objective, the application also provides a computer-readable storage medium, which includes an eyeball movement analysis program, the eyeball movement analysis program being executed by a processor to implement any step in the foregoing eyeball movement analysis method.

According to the eyeball movement analysis method and device and computer-readable storage medium disclosed in the application, the orbit feature points and the eyeball feature points are recognized from the real-time facial image, whether a region formed by eye feature points is a human eye region or not is judged at first, and if YES, movement information of the human eye is calculated according to the coordinates of the eye feature points. According to the method, an electric field change about the eyeball is not required to be detected, a change in an iris angle is also not required to be recognized, and analysis about the eye region and real-time capturing of the eyeball movement may be implemented only through the coordinates of the eyeball feature points.

Achievement of the objective, functional characteristics and advantages of the application will further be described in combination with embodiments and with reference to the accompanying drawings.

DETAILED DESCRIPTION OF ILLUSTRATED EMBODIMENTS

It is to be understood that the specific embodiments described herein are adopted not to limit the application but only to explain the application.

Figure 1:
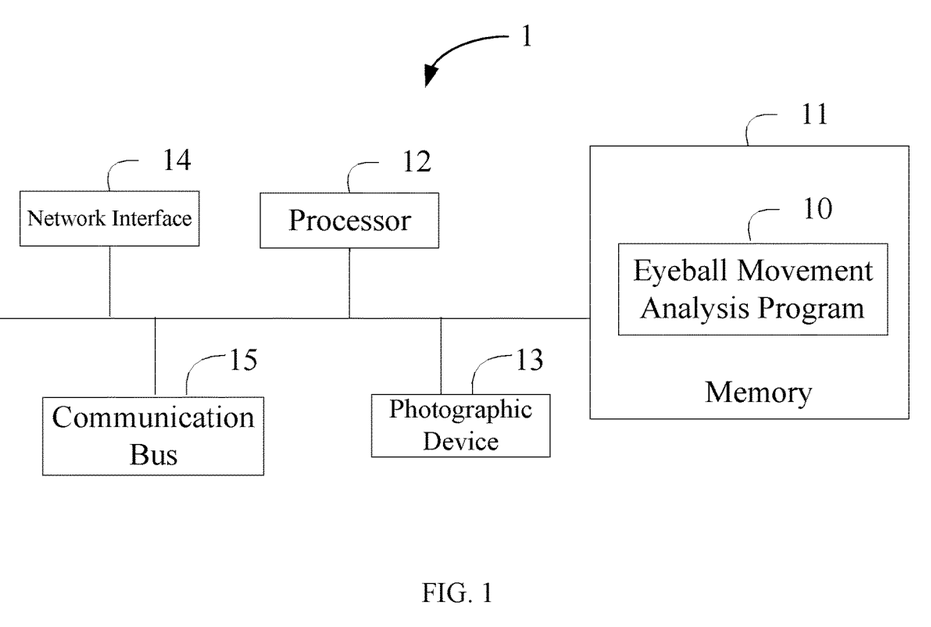
FIG. 1 is a schematic diagram of a preferred embodiment of an electronic device according to the application.

The application provides an electronic device 1. FIG. 1 is a schematic diagram of a preferred embodiment of an electronic device 1 according to the application.

In the embodiment, the electronic device 1 may be terminal equipment with an operation function such as a server, a smart phone, a tablet computer, a portable computer and a desktop computer.

The electronic device 1 includes a processor 12, a memory 11, a photographic device 13, a network interface 14 and a communication bus 15. Herein, the photographic device 13 is mounted at a specific place, for example, an office place and a monitoring region, shoots a target entering the specific place in real time to obtain a real-time image and transmits the shot real-time image to the processor 12 through a network. The network interface 14 may optionally include a standard wired interface and wireless interface (for example, wireless-fidelity (WI-FI) interface). The communication bus 15 is configured to implement connection and communication between these components.

The memory 11 includes at least one type of readable storage medium. The at least one type of readable storage medium may be a nonvolatile storage medium such as a flash memory, a hard disk, a multimedia card and a card type memory. In some embodiments, the readable storage medium may be an internal storage unit of the electronic device 1, for example, a hard disk of the electronic device 1. In some other embodiments, the readable storage medium may also be an external memory of the electronic device 1, for example, a plug-in type hard disk, smart media card (SMC), secure digital (SD) card and flash card configured on the electronic device 1.

In the embodiment, the readable storage medium of the memory 11 is usually configured to store an eyeball movement analysis program 10 installed in the electronic device 1, a facial image sample library, a human eye sample library, a constructed and trained eye mean shape and human eye classification model, and the like. The memory 11 may further be configured to temporally store data which has been output or is to be output.

In some embodiments, the processor 12 may be a central processing unit (CPU), a microprocessor or another data processing chip and is configured to run a program code stored in the memory 11 or process data, for example, executing the eyeball movement analysis program 10.

FIG. 1 only illustrates the electronic device 1 with the components 11-15 and the eyeball movement analysis program 10. However, it is to be understood that not all of the illustrated components are required to be implemented and, instead, more or fewer components may be implemented.

Optionally, the electronic device 1 may further include a user interface. The user interface may include an input unit such as a keyboard, a voice input device such as equipment with a voice recognition function like a microphone and a voice output device such as a sound and an earphone. Optionally, the user interface may also include a standard wired interface and wireless interface.

Optionally, the electronic device 1 may further include a display. The display may also be properly called a display screen or a display unit, and in some embodiments, may be a light-emitting diode (LED) display, a liquid crystal display, a touch liquid crystal display, an organic light-emitting diode (OLED) touch device and the like. The display is configured to display information processed in the electronic device 1 and configured to display a visual user interface.

Optionally, the electronic device 1 further includes a touch sensor. A region provided by the touch sensor for a touch operation of a user is called a touch region. In addition, the touch sensor may be a resistive touch sensor, a capacitive touch sensor and the like. Moreover, the touch sensor not only includes a contact type touch sensor and but also may include a proximity touch sensor and the like. Besides, the touch sensor may be a single sensor and may also be multiple sensors arranged in, for example, an array.

Furthermore, an area of the display of the electronic device 1 and an area of the touch sensor may be the same and may also be different. Optionally, the display and the touch sensor are arranged in a stacking manner to form a touch display screen. The device senses the touch operation triggered by the user on the basis of the touch display screen.

Optionally, the electronic device 1 may further include a Radio Frequency (RF) circuit, a sensor, an audio circuit and the like. No more elaborations will be made herein.

In the device embodiment shown in FIG. 1, the memory 11 used as a computer storage medium includes the eyeball movement analysis program 10. The processor 12 executes the eyeball movement analysis program 10 stored in the memory 11 to implement the following steps.

A real-time facial image acquisition step: a real-time image shot by the photographic device 13 is acquired, and a real-time facial image is extracted from the real-time image by use of a face recognition algorithm. When the photographic device 13 shoots the real-time image, the photographic device 13 sends the real-time image to the processor 12. After the processor 12 receives the real-time image, a picture size is acquired at first and a grayscale image with the same size is constructed. The acquired color image is converted into the grayscale image and, meanwhile, a memory space is created. A histogram of the grayscale image is equalized to reduce an information amount of the grayscale image and increase a detection speed. Then, a training library is loaded, a face in the image is detected, an object including facial information is returned, data about a position of the face is obtained and an amount of the data is recorded. A portrait region is finally acquired and stored. In such a manner, a real-time facial image extraction process is completed.

Specifically, the face recognition algorithm for extracting the real-time facial image from the real-time image may be a geometric-feature-based method, a local feature analysis method, an eigenface method, an elastic-model-based method, a neural network method and the like.

A feature point recognition step: the real-time facial image is input into a pretrained eye mean shape and $n_1$ orbit feature points and $n_2$ eyeball feature points representative of an eye position in the real-time facial image are recognized by use of the eye mean shape. After the real-time facial image is acquired and the trained eye mean shape for faces is called from the memory, the real-time facial image is aligned with the eye mean shape and then the real-time facial image is searched for 6 orbit feature points and 1 eyeball feature point matched with 6 orbit feature points and 1 eyeball feature point of the eye mean shape by use of a feature extraction algorithm.

Herein, the eye mean shape is obtained by the following steps.

A first sample library with n facial images is established and $n_1$ orbit feature points and $n_2$ eyeball feature points are marked in each facial image in the first sample library, the $(n_1+n_2)$ feature points in each facial image forming a shape feature vector S to obtain n shape feature vectors S of an eye. The orbit feature points and eyeball feature points in each facial image are manually marked.

A facial feature recognition model is trained by use of the n shape feature vectors S to obtain the eye mean shape about the faces. The facial feature recognition model is an ensemble of regression trees (ERT) algorithm. The ERT algorithm is represented by a formula as follows:

$$\hat{S}^{t+1} = \hat{S}^t + \tau_t(I, \hat{S}^t),$$

where t represents a concatenation sequence number and $\tau_t(\bullet,\bullet)$ represents a regressor of a present stage. Each regressor consists of multiple regression trees and an objective of training is to obtain these regression trees.

S (t) is a shape estimate of the present model. Each regressor $\tau_t(\bullet,\bullet)$ predicts an increment $\tau_t(I,\hat{S}^t)$ according to an input image I and S (t) and adds the increment to the present shape estimate to improve the present model. The regressors of each stage perform prediction according to the feature points. A training dataset is (I1, S1), . . . , (In, Sn), where I is the input sample image and S is a shape feature vector consisting of feature points in the sample image.

In a model training process, the number of the facial images in the first sample library is n. There is made such a hypothesis that each sample picture has 7 feature points (x, y), i.e., 6 orbit feature points and 1 eyeball feature point. The feature vector is $S=(x_1^i, x_2^i, x_3^i, x_5^i, x_6^i, x_7^i)$, i=1, 2, 3 . . . n, $x_1 \sim x_6$ representing x coordinates of the orbit feature points and $x_7$ representing an x coordinate of the eyeball feature point. Part of feature points of all the sample pictures (for example, 4 feature points are randomly selected from the 7 feature points of each sample picture) are extracted to train a first regression tree, a second tree is trained by use of residuals between predicted values of the first regression tree and true values (weighted averages of the 4 feature points extracted from each sample picture) of the part of feature points, and so on, when predicted values of an Nth trained tree and the true values of the part of feature points are close to zero, all regression trees of the ERT algorithm are obtained, the eye mean shape about the faces is obtained according to these regression trees and a model file and the sample library are stored in the memory. Since each sample for training the model is marked with the 6 orbit feature points and the 1 eyeball feature point, the trained eye mean shape for the faces may be configured to recognize the 6 orbit feature points and 1 eyeball feature point from the facial image.

In the embodiment, the feature extraction algorithm is a scale-invariant feature transform (SIFT) algorithm. According to the SIFT algorithm, local features of each eye feature point, for example, the 6 orbit feature points and the 1 eyeball feature point, are extracted from the eye mean shape for the faces, an eye feature point is selected as a reference feature point, and the real-time facial image is searched for a feature point with a local feature the same as or similar to that of the reference feature point, for example, whether a difference value of the local features of the two feature points is within a preset range or not is judged and, if YES, it is indicated that the feature point has a local feature the same as or similar to that of the reference feature point and is determined as an eye feature point. All of the eye feature points are found from the real-time facial image according to this principle. In another embodiment, the feature extraction algorithm may also be a speeded up robust features (SURF) algorithm, a local binary patterns (LBP) algorithm, a histogram of oriented gradients (HOG) algorithm and the like.

A human eye region recognition step: an eye region is determined according to the $n_1$ orbit feature points and the $n_2$ eyeball feature points, the eye region is input into a pretrained human eye classification model and whether the eye region is a human eye region or not is judged. Then, the determined eye region is input into the pretrained human eye classification model and whether the determined eye region is a human eye region or not is judged according to a result obtained by the model.

Herein, the human eye classification model is obtained by the following training steps.

m human eye positive sample images and m human eye negative sample images are collected. The human eye positive sample image refers to an eye sample including a human eye. Two eye parts may be cropped from the facial image sample library as eye samples. The human eye negative sample image refers to an image without an eye region. Multiple human eye positive sample images and negative sample images form a second sample library.

Local features of each human eye positive sample image and human eye negative sample image are extracted. HOG features of the human eye sample images are extracted by use of the feature extraction algorithm. Since color information in a human eye sample image plays a minor role, it is usually converted into a grayscale image, the whole image is normalized, gradients of the image in x coordinate and y coordinate directions of the image are calculated and a gradient direction value of each pixel position is accordingly calculated to capture a contour, a figure and some texture information and further weaken influence of light. Then, the whole image is divided into multiple cells (8*8 pixels), and a HOG is constructed for each cell for statistics about local image gradient information and quantization to obtain a feature description vector of a local image region. Next, the cells are combined into large blocks. Due to a change in light and a change in a foreground-background contrast, gradient strength changes in a large range and it is necessary to normalize the gradient strength to further compress the light, a shadow and an edge. Finally, HOG descriptors of all "blocks" are combined to form a final HOG feature description vector.

An SVM is trained by use of the positive and negative sample images in the second sample library and the extracted HOG features to obtain the human eye classification model.

An eyeball movement judgment step: if the eye region is a human eye region, a movement direction and movement distance of an eyeball in the real-time facial image are calculated according to x and y coordinates of the $n_1$ orbit feature points and $n_2$ eyeball feature points in the real-time facial image.

Specifically, the eyeball movement judgment step includes that:

a center coordinate of an orbit in the real-time facial image is calculated according to the x and y coordinates of the $n_1$ orbit feature points; and a positional relationship between a center of the orbit and each eyeball feature point is calculated to judge the movement direction and movement distance of the eyeball.

If there are 6 orbit feature points and 1 eyeball feature point in the eye feature points recognized from the real-time facial image, $(x_1, y_1)$, $(x_2, y_2)$, $(x_3, y_3)$, $(x_4, y_4)$, $(x_5, y_5)$ and $(x_6, y_6)$ being coordinates of the 6 orbit feature points respectively and $(x_7, y_7)$ being a coordinate of the eyeball feature point, and a judgment module 130 judges that the eye region is a human eye region, calculation formulas for the center coordinate (X, Y) of the orbit in the real-time facial image are as follows:

$$centerX=(x_1+x_2+x_3+x_4+x_5+x_6)/6, \text{ and}$$

$$centerY=(y_1+y_2+y_3+y_4+y_5+y_6)/6.$$

By use of the center coordinate (X, Y) of the orbit and the coordinate $(x_7, y_7)$ of the eyeball feature point, the positional relationship therebetween is calculated and the movement direction and movement distance of the eyeball are judged through the following calculation formulae:

$$\Delta x=x_7-centerX \text{ and } \Delta y=y_7-centerY,$$

where values of $\Delta x$ and $\Delta_y$ represent the movement distance of the eyeball in a certain direction (left-right and top-bottom).

For example, if $\Delta_x>0$, it is indicated that the eyeball moves leftwards and, if $\Delta_x<0$, it is indicated that the eyeball moves rightwards; and if $\Delta_y>0$, it is indicated that the eyeball moves upwards and, if $\Delta_y<0$, it is indicated that the eyeball moves downwards.

Similarly, when $n_2>1$, that is, there are multiple eyeball feature points in the eye mean shape, the multiple eyeball feature points may be recognized from the real-time facial image, then a mean value of the x and y coordinates of the multiple eyeball feature points is taken as a center coordinate of the eyeball and a difference value with the center coordinate of the orbit is calculated.

A prompting step: when the human eye classification model judges that the eye region is not a human eye region, such a prompt that no human eye region is detected in the present real-time image and no eyeball movement can be judged is made, and the real-time image capturing step is re-executed to capture a next real-time image. After the eye region determined through the 6 orbit feature points and the 1 eyeball feature point is input into the human eye classification model, if it is judged according to the result of the model that the eye region is not a human eye region, such a prompt that no human eye region is recognized and the next eyeball movement information calculation step cannot be performed may be made. Meanwhile, the real-time facial image acquisition step is re-executed to reacquire a real-time image shot by the photographic device 13 and subsequent steps are executed.

According to the electronic device 1 disclosed in the embodiment, the real-time facial image is extracted from the real-time image, the orbit feature points and eyeball feature points in the real-time facial image are recognized by use of the eye mean shape, the eye region determined through the feature points is analyzed by use of the human eye classification model, and if the eye region is a human eye region, movement information of the eyeball in the real-time facial image is calculated according to the coordinates of the orbit feature points and the eyeball feature points to implement analysis about the eye region and real-time capturing of an eyeball movement.

Figure 2:
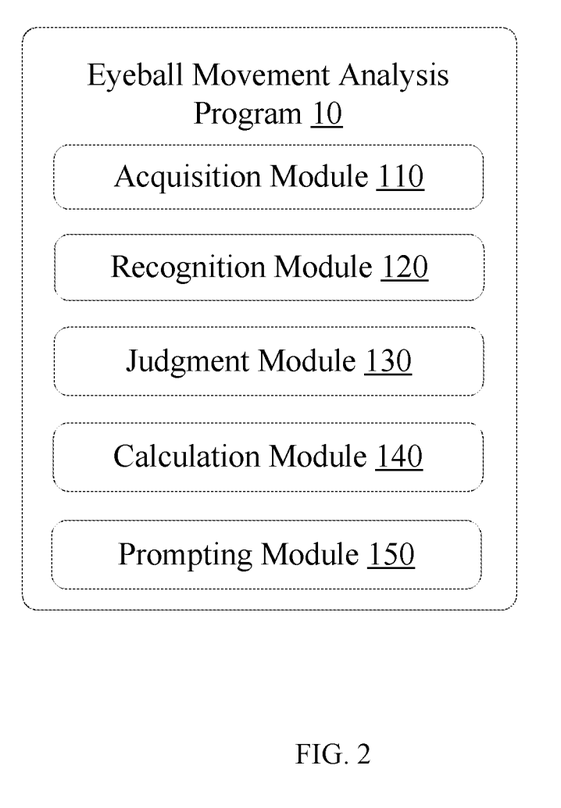
FIG. 2 is a schematic diagram of modules of an eyeball movement analysis program in FIG. 1.

In another embodiment, the eyeball movement analysis program 10 may further be divided into one or more modules and the one or more modules are stored in the memory 11 and executed by the processor 12 to implement the application. The modules in the application refer to a series of computer program instruction segments capable of realizing specific functions. FIG. 2 is a schematic diagram of modules of an eyeball movement analysis program 10 in FIG. 1.

In the embodiment, the eyeball movement analysis program 10 may be divided into an acquisition module 110, a recognition module 120, a judgment module 130, a calculation module 140 and a prompting module 150. Functions or operation steps implemented by the modules 110-150 are similar to the above and will not be elaborated herein. Exemplarily, the acquisition module 110 is configured to acquire a real-time image shot by a photographic device 13 and extract a real-time facial image from the real-time image by use of a face recognition algorithm.

The recognition module 120 is configured to input the real-time facial image into a pretrained eye mean shape and recognizing $n_1$ orbit feature points and $n_2$ eyeball feature points representative of an eye position in the real-time facial image by use of the eye mean shape.

The judgment module 130 is configured to determine an eye region according to the $n_1$ orbit feature points and the $n_2$ eyeball feature points, input the eye region into a pretrained human eye classification model and judge whether the eye region is a human eye region or not.

The calculation module 140 is configured to, if the eye region is a human eye region, calculate a movement direction and movement distance of an eyeball in the real-time facial image according to x and y coordinates of the $n_1$ orbit feature points and $n_2$ eyeball feature points in the real-time facial image.

The prompting module 150 is configured to, when the human eye classification model judges that the eye region is not a human eye region, make such a prompt that no human eye region is detected in the present real-time image and no eyeball movement can be judged and return to a real-time image capturing step to capture a next real-time image.

Figure 3:
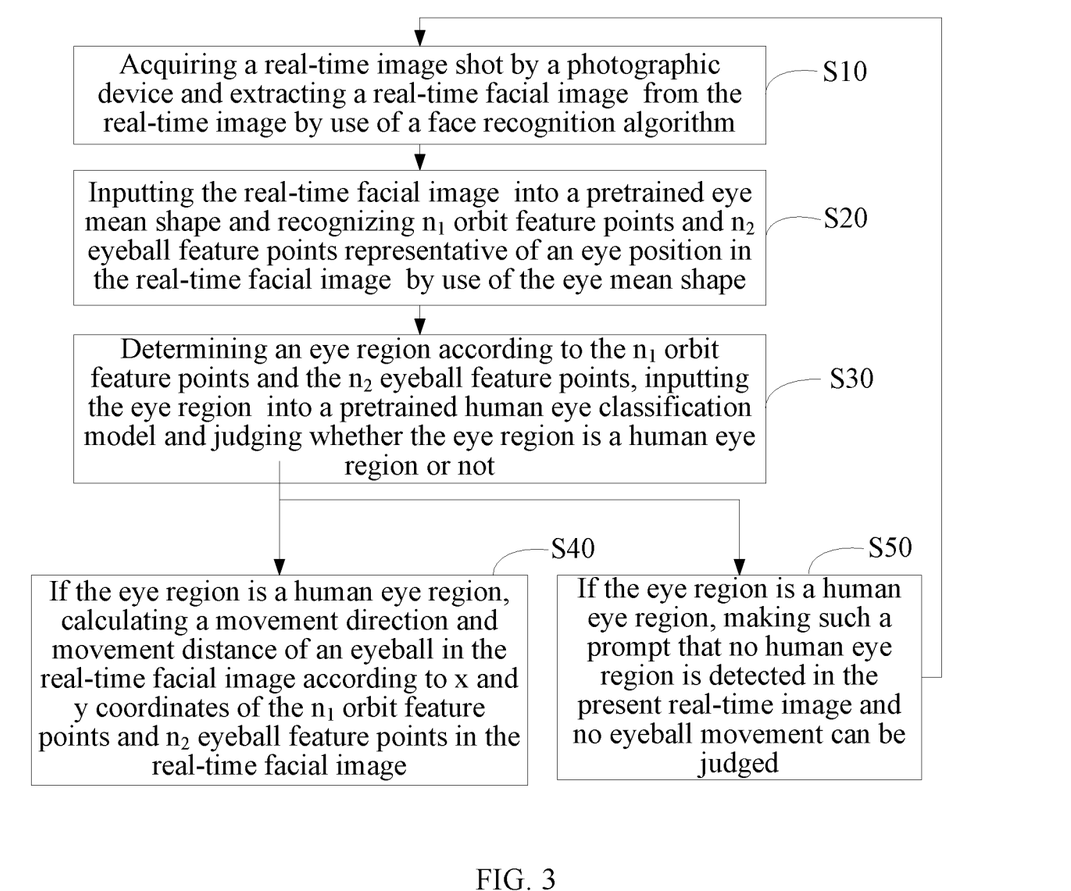
FIG. 3 is a flowchart of a first embodiment of an eyeball movement analysis method according to the application.

In addition, the application also provides an eyeball movement analysis method. FIG. 3 is a flowchart of a preferred embodiment of an eyeball movement analysis method according to the application. The method may be executed by a device and the device may be implemented by software and/or hardware.

In the embodiment, the eyeball movement analysis method includes S10-S50.

In S10, a real-time image shot by a photographic device is acquired and a real-time facial image is extracted from the real-time image by use of a face recognition algorithm.

When the photographic device shoots the real-time image, the photographic device sends the real-time image to a processor. After the processor receives the real-time image, a picture size is acquired at first and a grayscale image with the same size is constructed. The acquired color image is converted into the grayscale image and, meanwhile, a memory space is created. A histogram of the grayscale image is equalized to reduce an information amount of the grayscale image and increase a detection speed. Then, a training library is loaded, a face in the image is detected, an object including facial information is returned, data about a position of the face is obtained and an amount of the data is recorded. A portrait region is finally acquired and stored. In such a manner, a real-time facial image extraction process is completed.

Specifically, the face recognition algorithm for extracting the real-time facial image from the real-time image may be a geometric-feature-based method, a local feature analysis method, an eigenface method, an elastic-model-based method, a neural network method and the like.

In S20, the real-time facial image is input into a pretrained eye mean shape and $n_1$ orbit feature points and $n_2$ eyeball feature points representative of an eye position in the real-time facial image are recognized by use of the eye mean shape;

After the real-time facial image is acquired and the trained eye mean shape for faces is called from the memory, the real-time facial image is aligned with the eye mean shape and then the real-time facial image is searched for 6 orbit feature points and 1 eyeball feature point matched with 6 orbit feature points and 1 eyeball feature point of the eye mean shape by use of a feature extraction algorithm.

Herein, the eye mean shape is obtained by the following steps.

A first sample library with n facial images is established and $n_1$ orbit feature points and $n_2$ eyeball feature points are marked in each facial image in the first sample library, the $(n_1+n_2)$ feature points in each facial image forming a shape feature vector S to obtain n shape feature vectors S of an eye. The orbit feature points and eyeball feature points in each facial image are manually marked.

A facial feature recognition model is trained by use of the n shape feature vectors S to obtain the eye mean shape about the faces. The facial feature recognition model is an ERT algorithm. The ERT algorithm is represented by a formula as follows:

$$\hat{S}^{t+1} = \hat{S}^t = \tau_t(I, \hat{S}^t),$$

where t represents a concatenation sequence number and represents $\tau_t(\bullet,\bullet)$ a regressor of a present stage. Each regressor consists of multiple regression trees and an objective of training is to obtain these regression trees.

S (t) is a shape estimate of the present model. Each regressor $\tau_t(\bullet,\bullet)$ predicts an increment $\tau_t(I, \hat{S}^t)$ according to an input image I and S (t) and adds the increment to the present shape estimate to improve the present model. The regressors of each stage perform prediction according to the feature points. A training dataset is (I1, S1), . . . , (In, Sn), where I is the input sample image and S is a shape feature vector consisting of feature points in the sample image.

In a model training process, the number of the facial images in the first sample library is n. There is made such a hypothesis that each sample picture has 7 feature points (x, y), i.e., 6 orbit feature points and 1 eyeball feature point. The feature vector is $S=(x_1^i, x_2^i, x_3^i, x_4^i, x_5^i, x_6^i, x_7^i)$, i=1, 2, 3 . . . n, $x_1$~$x_6$ representing x coordinates of the orbit feature points and $x_7$ representing an x coordinate of the eyeball feature point. Part of feature points of all the sample pictures (for example, 4 feature points are randomly selected from the 7 feature points of each sample picture) are extracted to train a first regression tree, a second tree is trained by use of residuals between predicted values of the first regression tree and true values (weighted averages of the 4 feature points extracted from each sample picture) of the part of feature points, and so on, when predicted values of an Nth trained tree and the true values of the part of feature points are close to zero, all regression trees of the ERT algorithm are obtained, the eye mean shape about the faces is obtained according to these regression trees and a model file and the sample library are stored in the memory. Since each sample for training the model is marked with the 6 orbit feature points and the 1 eyeball feature point, the trained eye mean shape for the faces may be configured to recognize the 6 orbit feature points and 1 eyeball feature point from the facial image.

In the embodiment, the feature extraction algorithm is a SIFT algorithm. According to the SIFT algorithm, local features of each eye feature point, for example, the 6 orbit feature points and the 1 eyeball feature point, are extracted from the eye mean shape for the faces, an eye feature point is selected as a reference feature point, and the real-time facial image is searched for a feature point with a local feature the same as or similar to that of the reference feature point, for example, whether a difference value of the local features of the two feature points is within a preset range or not is judged and, if YES, it is indicated that the feature point has a local feature the same as or similar to that of the reference feature point and is determined as an eye feature point. All of the eye feature points are found from the real-time facial image according to this principle. In another embodiment, the feature extraction algorithm may also be a SURF algorithm, an LBP algorithm, a HOG algorithm and the like.

In S30, an eye region is determined according to the $n_1$ orbit feature points and the $n_2$ eyeball feature points, the eye region is input into a pretrained human eye classification model and whether the eye region is a human eye region or not is judged. Then, the determined eye region is input into the pretrained human eye classification model and whether the determined eye region is a human eye region or not is judged according to a result obtained by the model.

Herein, the human eye classification model is obtained by the following training steps.

m human eye positive sample images and m human eye negative sample images are collected. The human eye positive sample image refers to an eye sample including a human eye.

Two eye parts may be cropped from the facial image sample library as eye samples. The human eye negative sample image refers to an image without an eye region. Multiple human eye positive sample images and negative sample images form a second sample library.

Local features of each human eye positive sample image and human eye negative sample image are extracted. HOG features of the human eye sample images are extracted by use of the feature extraction algorithm. Since color information in a human eye sample image plays a minor role, it is usually converted into a grayscale image, the whole image is normalized, gradients of the image in x coordinate and y coordinate directions of the image are calculated and a gradient direction value of each pixel position is accordingly calculated to capture a contour, a figure and some texture information and further weaken influence of light. Then, the whole image is divided into multiple cells (8*8 pixels), and a HOG is constructed for each cell for statistics about local image gradient information and quantization to obtain a feature description vector of a local image region. Next, the cells are combined into large blocks. Due to a change in light and a change in a foreground-background contrast, gradient strength changes in a large range and it is necessary to normalize the gradient strength to further compress the light, a shadow and an edge. Finally, HOG descriptors of all "blocks" are combined to form a final HOG feature description vector.

An SVM is trained by use of the positive and negative sample images in the second sample library and the extracted HOG features to obtain the human eye classification model.

In S40, if the eye region is a human eye region, a movement direction and movement distance of an eyeball in the real-time facial image are calculated according to x and y coordinates of the $n_1$ orbit feature points and $n_2$ eyeball feature points in the real-time facial image.

Figure 4:
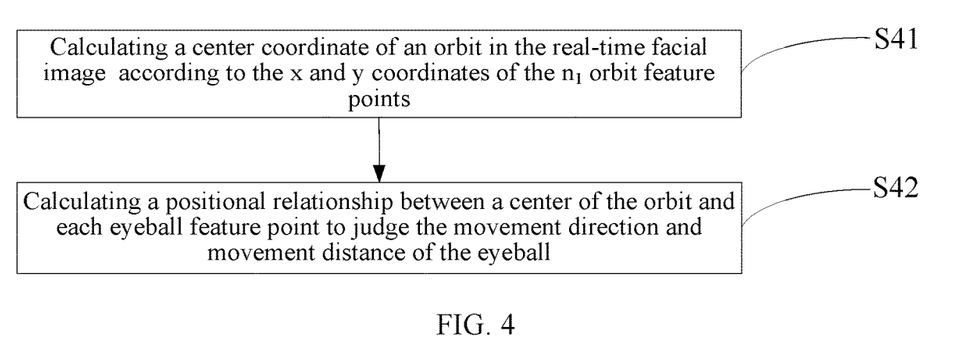
FIG. 4 is a detailed flowchart of S40 of an eyeball movement analysis method according to the application.

FIG. 4 is a detailed flowchart of S40 in an eyeball movement analysis method according to the application. Specifically, S40 includes the following steps:

In S41, a center coordinate of an orbit in the real-time facial image is calculated according to the x and y coordinates of the $n_1$ orbit feature points.

In S42, a positional relationship between a center of the orbit and each eyeball feature point is calculated to judge the movement direction and movement distance of the eyeball.

If there are 6 orbit feature points and 1 eyeball feature point in the eye feature points recognized from the real-time facial image, $(x_1, y_1)$, $(x_2, y_2)$, $(x_3, y_3)$, $(x_4, y_4)$, $(x_5, y_5)$ and $(x_6, y_6)$ being coordinates of the 6 orbit feature points respectively and $(x_7, y_7)$ being a coordinate of the eyeball feature point, and a judgment module 130 judges that the eye region is a human eye region, calculation formulas for the center coordinate (X, Y) of the orbit in the real-time facial image are as follows:

$$centerX=(x_1+x_2+x_3+x_4+x_5+x_6)/6, \text{ and}$$

$$centerY=(y_1+y_2+y_3+y_4+y_5+y_6)/6.$$

By use of the center coordinate (X, Y) of the orbit and the coordinate $(x_7, y_7)$ of the eyeball feature point, the positional relationship therebetween is calculated and the movement direction and movement distance of the eyeball are judged through the following calculation formulae:

$$\Delta_x=x_7-centerX \text{ and } \Delta_y=y_7-centerY,$$

where values of $\Delta x$ and $\Delta_y$ represent the movement distance of the eyeball in a certain direction (left-right and top-bottom).

For example, if $\Delta_x>0$, it is indicated that the eyeball moves leftwards and, if $\Delta_x<0$, it is indicated that the eyeball moves rightwards; and if $\Delta_y>0$, it is indicated that the eyeball moves upwards and, if $\Delta_y<0$, it is indicated that the eyeball moves downwards.

Similarly, when $n_2>1$, that is, there are multiple eyeball feature points in the eye mean shape, the multiple eyeball feature points may be recognized from the real-time facial image, then a mean value of the x and y coordinates of the multiple eyeball feature points is taken as a center coordinate of the eyeball and a difference value with the center coordinate of the orbit is calculated.

In S50, when the human eye classification model judges that the eye region is not a human eye region, such a prompt that no human eye region is detected in the present real-time image and no eyeball movement can be judged is made, and the real-time image capturing step is re-executed to capture a next real-time image.

After the eye region determined through the 6 orbit feature points and the 1 eyeball feature point is input into the human eye classification model, if it is judged according to the result of the model that the eye region is not a human eye region, such a prompt that no human eye region is recognized and the next eyeball movement information calculation step cannot be performed may be made. Meanwhile, the S10 is re-executed to reacquire a real-time image shot by the photographic device and subsequent steps are executed.

According to the eyeball movement analysis method disclosed in the embodiment, the orbit feature points and eyeball feature points in the real-time facial image are recognized by use of the eye mean shape, the eye region determined through the feature points is analyzed by use of the human eye classification model, and if the eye region is a human eye region, movement information of the eyeball in the real-time facial image is calculated according to the coordinates of the orbit feature points and the eyeball feature points to implement analysis about the eye region and real-time capturing of an eyeball movement.

Moreover, an embodiment of the application also discloses a computer-readable storage medium, which includes an eyeball movement analysis program, the eyeball movement analysis program being executed by a processor to implement the following operations:

a real-time facial image acquisition step: a real-time image shot by a photographic device is acquired and a real-time facial image from the real-time image is extracted by use of a face recognition algorithm;

a feature point recognition step: the real-time facial image is input into a pretrained eye mean shape and $n_1$ orbit feature points and $n_2$ eyeball feature points representative of an eye position in the real-time facial image are recognized by use of the eye mean shape;

a human eye region recognition step: an eye region is determined according to the $n_1$ orbit feature points and the $n_2$ eyeball feature points, the eye region is input into a pretrained human eye classification model and whether the eye region is a human eye region or not is judged; and an eyeball movement judgment step: if the eye region is a human eye region, a movement direction and movement distance of an eyeball in the real-time facial image are calculated according to x and y coordinates of the $n_1$ orbit feature points and $n_2$ eyeball feature points in the real-time facial image.

Optionally, the eyeball movement judgment step includes that:

a center coordinate of an orbit in the real-time facial image is calculated according to the x and y coordinates of the $n_1$ orbit feature points; and a positional relationship between a center of the orbit and each eyeball feature point is calculated to judge the movement direction and movement distance of the eyeball.

Optionally, the eyeball movement analysis program is executed by the processor to further implement the following operation:

a prompting step: when the human eye classification model judges that the eye region is not a human eye region, such a prompt that no human eye region is detected in the present real-time image and no eyeball movement can be judged is made, and the real-time image capturing step is re-executed to capture a next real-time image.

Specific implementation modes of the computer-readable storage medium of the application are substantially the same as the specific implementation modes of the eyeball movement analysis method and will not be elaborated herein.

It is to be noted that terms "include" and "contain" or any other variant thereof in the disclosure are intended to cover nonexclusive inclusions, so that a process, device, object or method including a series of elements not only includes those elements but also includes other elements which are not listed clearly or further includes elements intrinsic to the process, the device, the object or the method. Under the condition of no more restrictions, an element defined by a statement "including a/an . . . " does not exclude existence of the same other element in a process, device, object or method including the element.

The foregoing numbering of the embodiments of the application is intended for description only, and is not indicative of the pros and cons of these embodiments. By the description of the foregoing embodiments, it will be evident to those skilled in the art that the methods of the embodiments can be implemented by means of software plus the necessary general-purpose hardware platform; and they can of course be implemented by hardware, but in many cases the former will be more advantageous. Based on such an understanding, the essential technical solution of the application, or the portion that contributes to the prior art may be embodied as software products. Computer software products can be stored in a storage medium (e.g., a read-only memory (ROM)/random access memory (RAM), a magnetic disk, an optical disc), including multiple instructions that, when executed, can cause terminal equipment (e.g., a mobile phone, a computer, a server, a network device), to execute the methods described in the various embodiments of the application.

The above is only the preferred embodiment of the application and therefore is not intended as limiting the patentable scope of the application. Any equivalent configurational or flow transformations that are made taking advantage of the application and that are used directly or indirectly in any other related technical field shall all fall in the scope of protection of the application.

What is claimed is:

1. An electronic device, comprising: a memory, a processor and a photographic device, the memory comprising an eyeball movement analysis program and the eyeball movement analysis program being executed by the processor to implement the following steps of:

a real-time facial image acquisition step: acquiring a real-time image shot by the photographic device and extracting a real-time facial image from the real-time image by use of a face recognition algorithm;

a feature point recognition step: inputting the real-time facial image into a pretrained eye mean shape and recognizing $n_1$ orbit feature points and $n_2$ eyeball feature points representative of an eye position in the real-time facial image by use of the eye mean shape, wherein the training steps for the eye mean shape comprising:

establishing a first sample library with n facial images and marking $n_1$ orbit feature points and $n_2$ eyeball feature points in each facial image in the first sample library, the $(n_1+n_2)$ feature points in each facial image forming a shape feature vector S to obtain n shape feature vectors S of an eye; and training a facial feature recognition model by use of the n shape feature vectors S to obtain the eye mean shape about faces;

a human eye region recognition step: determining an eye region according to the $n_1$ orbit feature points and the $n_2$ eyeball feature points, inputting the eye region into a pretrained human eye classification model and judging whether the eye region is a human eye region or not; and an eyeball movement judgment step: if the eye region is a human eye region, calculating a movement direction and movement distance of an eyeball in the real-time facial image according to x and y coordinates of the $n_1$ orbit feature points and $n_2$ eyeball feature points in the real-time facial image;

wherein the training steps for the human eye classification model comprising:

collecting m human eye positive sample images and m human eye negative sample images; extracting local features of each human eye positive sample image and human eye negative sample image; and training a Support Vector Machine (SVM) by use of the human eye positive sample images, the human eye negative sample images and the local features thereof to obtain the human eye classification model, wherein the facial feature recognition model is an ensemble of regression trees (ERT) algorithm and represented by a formula as follows:

$$\hat{S}^{t+1}=\hat{S}^t+\tau_t(I,\hat{S}^t),$$

where t represents a concatenation sequence number, $\tau_t(\cdot,\cdot)$ represents a regressor of a present stage and S (t) is a shape estimate of a present model each regressor $\tau_t(\cdot,\cdot)$ predicts an increment $\tau_t(I,\hat{S}^t)$ according to an input present image I and S (t); and in a model training process, part of feature points of all sample pictures are extracted to train a first regression tree, a second tree is trained by use of residuals between predicted values of the first regression tree and true values of the part of feature points, and so on, when residuals of predicted values of an Nth trained tree and the true values of the part of feature points are close to zero, all regression trees of the ERT algorithm are obtained, and the eye mean shape for the faces is obtained according to these regression trees.

2. The electronic device of claim 1, wherein the eyeball movement judgment step comprises:
   calculating a center coordinate of an orbit in the real-time facial image according to the x and y coordinates of the $n_1$ orbit feature points; and
   calculating a positional relationship between a center of the orbit and each eyeball feature point to judge the movement direction and movement distance of the eyeball.

3. The electronic device of claim 1, wherein the eyeball movement analysis program is executed by the processor to further implement the following step:
   a prompting step: when the human eye classification model judges that the eye region is not a human eye region, making such a prompt that no human eye region is detected in the present real-time image and no eyeball movement can be judged, and returning to the real-time image capturing step to capture a next real-time image.

4. An eyeball movement analysis method, comprising:
   a real-time facial image acquisition step: acquiring a real-time image shot by the photographic device and extracting a real-time facial image from the real-time image by use of a face recognition algorithm;
   a feature point recognition step: inputting the real-time facial image into a pretrained eye mean shape and recognizing $n_1$ orbit feature points and $n_2$ eyeball feature points representative of an eye position in the real-time facial image by use of the eye mean shape, wherein the training steps for the eye mean shape comprising: establishing a first sample library with n facial images and marking $n_1$ orbit feature points and $n_2$ eyeball feature points in each facial image in the first sample library, the $(n_1+n_2)$ feature points in each facial image forming a shape feature vector S to obtain n shape feature vectors S of an eye; and training a facial feature recognition model by use of the n shape feature vectors S to obtain the eye mean shape about faces;
   a human eye region recognition step: determining an eye region according to the $n_1$ orbit feature points and the $n_2$ eyeball feature points, inputting the eye region into a pretrained human eye classification model and judging whether the eye region is a human eye region or not; and
   an eyeball movement judgment step: if the eye region is a human eye region, calculating a movement direction and movement distance of an eyeball in the real-time facial image according to x and y coordinates of the $n_1$ orbit feature points and $n_2$ eyeball feature points in the real-time facial image;
   wherein the training steps for the human eye classification model comprising:
   collecting m human eye positive sample images and m human eye negative sample images; extracting local features of each human eye positive sample image and human eye negative sample image; and training a Support Vector Machine (SVM) by use of the human eye positive sample images, the human eye negative sample images and the local features thereof to obtain the human eye classification model;
   wherein the facial feature recognition model is an ensemble of regression trees (ERT) algorithm and is represented by a formula as follows:

$$\hat{S}^{t+1}=\hat{S}^t+\tau_t(I,\hat{S}^t),$$

where t represents a concatenation sequence number, $\tau_t(\cdot,\cdot)$ represents a regressor of a present stage and S (t) is a shape estimate of a present model; each regressor $\tau_t(\cdot,\cdot)$ predicts an increment $\tau_t(I,\hat{S}^t)$ according to an input present image I and S (t); and in a model training process, part of feature points of all sample pictures are extracted to train a first regression tree, a second tree is trained by use of residuals between predicted values of the first regression tree and true values of the part of feature points, and so on, when residuals of predicted values of an Nth trained tree and the true values of the part of feature points are close to zero all regression trees of the ERT algorithm are obtained, and the eye mean shape for the faces is obtained according to these regression trees.

5. A computer-readable storage medium, comprising an eyeball movement analysis program, the eyeball movement analysis program being executed by a processor to implement all steps of the eyeball movement analysis method of claim 4.

6. The eyeball movement analysis method of claim 4, wherein the eyeball movement judgment step comprises:
   calculating a center coordinate of an orbit in the real-time facial image according to the x and y coordinates of the $n_1$ orbit feature points; and
   calculating a positional relationship between a center of the orbit and each eyeball feature point to judge the movement direction and movement distance of the eyeball.

7. A computer-readable storage medium, comprising an eyeball movement analysis program, the eyeball movement analysis program being executed by a processor to implement all steps of the eyeball movement analysis method of claim 6.

8. The eyeball movement analysis method of claim 6, further comprising:
   a prompting step: when the human eye classification model judges that the eye region is not a human eye region, making such a prompt that no human eye region is detected in the present real-time image and no eyeball movement can be judged, and returning to the real-time image capturing step to capture a next real-time image.

9. A computer-readable storage medium, comprising an eyeball movement analysis program, the eyeball movement analysis program being executed by a processor to implement all steps of the eyeball movement analysis method of claim 8.

* * * * *